(12) United States Patent
Walker et al.

(10) Patent No.: US 8,478,429 B2
(45) Date of Patent: Jul. 2, 2013

(54) EXTENDABLE/RETRACTABLE FIXATION LEAD WITH DISTAL TRAVELLING SEAL AND RELATED DEVICES

(75) Inventors: Joseph Walker, Shoreview, MN (US); Ronald W. Heil, Jr., Roseville, MN (US); G. Shantanu Reddy, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 44 days.

(21) Appl. No.: 13/253,345

(22) Filed: Oct. 5, 2011

(65) Prior Publication Data

US 2012/0165914 A1    Jun. 28, 2012

Related U.S. Application Data

(60) Provisional application No. 61/427,676, filed on Dec. 28, 2010.

(51) Int. Cl.
*A61N 1/00* (2006.01)

(52) U.S. Cl.
USPC ........................................... 607/122

(58) Field of Classification Search
USPC ................................. 607/115–131
See application file for complete search history.

(56) References Cited

U.S. PATENT DOCUMENTS

| | | | |
|---|---|---|---|
| 5,456,708 | A | 10/1995 | Doan et al. |
| 5,902,329 | A | 5/1999 | Hoffmann et al. |
| 6,240,321 | B1 | 5/2001 | Janke et al. |
| 6,813,521 | B2 | 11/2004 | Bischoff et al. |
| 6,931,285 | B2 | 8/2005 | Bischoff |
| 7,218,971 | B2 | 5/2007 | Heil, Jr. et al. |
| 7,412,290 | B2 | 8/2008 | Janke et al. |
| 8,391,997 | B2 | 3/2013 | Jorgensen et al. |
| 2007/0225772 | A1 | 9/2007 | Lahti et al. |
| 2007/0233216 | A1* | 10/2007 | Liu et al. ................ 607/122 |
| 2010/0305672 | A1 | 12/2010 | Felling et al. |
| 2010/0331943 | A1* | 12/2010 | Jorgensen et al. .......... 607/127 |

* cited by examiner

*Primary Examiner* — Scott Getzow
(74) *Attorney, Agent, or Firm* — Faegre Baker Daniels LLP (57) ABSTRACT

An implantable lead having a distal assembly including a coupler, a fixation helix secured to the coupler, a housing in which the fixation helix and the coupler are disposed, and a resilient seal that is fixedly secured to the coupler between proximal and distal ends thereof and able to translate with the coupler relative to the housing. The seal is positioned to sealingly engage an internal surface of the housing. When the coupler is translated such that the fixation helix is in a fully extended position, the seal is positioned to substantially seal off the housing to prevent tissue ingrowth.

20 Claims, 6 Drawing Sheets

EXTENDABLE/RETRACTABLE FIXATION LEAD WITH DISTAL TRAVELLING SEAL AND RELATED DEVICES

RELATED APPLICATION

This application claims the benefit under 35 U.S.C. 119(e) of U.S. Provisional Patent Application Ser. No. 61/427,676, filed on Dec. 28, 2010, which is incorporated herein by reference in its entirety.

TECHNICAL HELD

The present invention relates to implantable medical devices and relates more particularly to leads used with implantable medical devices for cardiac rhythm management (CRM) systems.

BACKGROUND

Various types of medical electrical leads for use in CRM and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

In Example 1, an implantable lead comprising a flexible body and a distal assembly. The flexible body extends between a proximal end and a distal end. The distal assembly is coupled to the distal end of the body and includes a housing, a coupler, a helical electrode, and a resilient seal. The housing has a wall having an external surface and an internal surface defining an inner lumen, a distal end and a proximal end. The proximal end is fixedly coupled to the distal end of the body. The housing further has an axial shoulder extending radially inward relative to the internal surface at or near the distal end of the housing. The coupler is rotatably disposed within the housing and has a proximal end and a distal end. The helical electrode is fixedly secured to the distal end of the coupler, and the coupler and the helical electrode are configured to translate relative to the housing between a retracted position and a fully extended position. The resilient seal is fixedly secured to the coupler between the proximal and distal ends thereof and able to translate with the coupler relative to the housing. The seal is positioned to sealingly engage the internal surface of the housing wall, wherein when the helical electrode is in the fully extended position, the seal is positioned proximate the shoulder of the housing to substantially seal off the inner lumen of the housing.

In Example 2, the implantable lead according to Example 1, wherein the seal is in contact with the shoulder when the helical electrode is in the fully extended position.

In Example 3, the implantable lead according to Example 1 or 2, and further comprising a groove in the inner surface of the housing wall, and a distal flange and a proximal flange attached to the coupler that surround the seal, wherein the seal sits in the groove, and when the conductor member is translated such that the helical electrode is in the fully extended position, the distal flange is in contact with the shoulder of the housing.

In Example 4, the implantable lead according to Examples 1-3, wherein the seal comprises an O-ring.

In Example 5, the implantable lead according to Examples 1-4, further comprising a low-voltage electrode that is mounted on the body proximal to the helical electrode, and a high-voltage electrode that is mounted on the body proximal to the low-voltage electrode, wherein the body is configured such that the distance between the low-voltage electrode and the high-voltage electrode is about 12 mm.

In Example 6, the implantable lead according to Examples 1-5, further comprising a low-voltage electrode that comprises a flexible coil that is mounted on the body proximal to the helical electrode, and a high-voltage electrode that is mounted on the body proximal to the low-voltage electrode, such that a first portion of the flexible body is located between the flexible coil and the helical electrode and a second portion of flexible body is located between the flexible coil and the high voltage electrode.

In Example 7, the implantable lead according to Examples 1-6, wherein the seal provides an at least substantially fluid-tight seal with the housing.

In Example 8, an implantable lead comprising a flexible body and a distal assembly. The flexible body extends between a proximal end and a distal end. The distal assembly is coupled to the distal end of the body, and includes a housing, a coupler, a drug eluting collar, a helical electrode, and a resilient seal. The housing has a wall having an external surface and an internal surface defining an inner lumen, a distal end and a proximal end, the proximal end fixedly coupled to the distal end of the body. The coupler is rotatably disposed within the housing and has a proximal end and a distal end. The drug-eluting collar is disposed at the distal end of the housing, and includes a portion extending radially inward relative to the internal surface of the housing wall. The helical electrode is fixedly secured to the coupler, wherein the coupler and the helical electrode are configured to translate relative to the housing between a retracted position and a fully extended position. The resilient seal is fixedly secured to the coupler between the proximal and distal ends thereof and is able to translate with the coupler relative to the housing. The seal is positioned to sealingly engage the internal surface of the housing wall, wherein when the helical electrode is in the fully extended position, the seal is positioned proximate the drug-eluting collar to substantially seal off the inner lumen of the housing.

In Example 9, the implantable lead according to Example 8, wherein the seal is in contact with the drug-eluting collar when the helical electrode is in the fully extended position.

In Example 10, the implantable lead according to Example 8 or 9, further comprising a groove in the inner surface of the housing wall, and a distal flange and a proximal flange attached to the coupler that surround the seal, wherein the seal sits in the groove, and when the conductor member is translated such that the helical electrode is in the fully extended position, the distal flange is in contact with the drug-eluting collar.

In Example 11, the implantable lead according to Examples 8-10, wherein the seal comprises an O-ring.

In Example 12, the implantable lead according to Examples 8-11, further comprising a low-voltage electrode that is mounted on the body proximal to the helical electrode, and a high-voltage electrode that is mounted on the body proximal to the low-voltage electrode, and the body is configured such that the distance between the low-voltage electrode and the high-voltage electrode is about 12 mm.

In Example 13, the implantable lead according to Examples 8-12, further comprising a low-voltage electrode that comprises a flexible coil that is mounted on the body proximal to the helical electrode, and a high-voltage electrode that is mounted on the body proximal to the low-voltage electrode, such that a first portion of the flexible body is located between the flexible coil and the helical electrode and a second portion of flexible body is located between the flexible coil and the high voltage electrode.

In Example 14, the implantable lead according to Examples 8-13, wherein the drug-eluting collar comprises an elastomer and a steroid.

In Example 15, the implantable lead according to Example 8-14, wherein the seal provides an at least substantially fluid-tight seal with the drug-eluting collar.

In Example 16, an implantable lead configured to carry an electrical signal, the implantable lead comprising a flexible body, and a distal assembly. The flexible body extends between a proximal end and a distal end, and is configured to carry an electrical signal from the proximal end to the distal end. The distal assembly is coupled to the distal end of the body and includes a housing, a coupler, a fixation helix and a resilient seal. The housing has a distal region and a proximal region, the proximal region fixedly coupled to the distal end of the body, the distal region including a distal end. The coupler is rotatably disposed within the housing and has a proximal region and a distal region. The fixation helix is attached to the coupler and is able to translate with the coupler between a retracted position and a fully extended position. The resilient seal is disposed on the coupler and between the coupler and the housing, and is able to translate with the coupler relative to the housing and sealingly engage the housing. When the coupler is translated such that the fixation helix is in the fully extended position, the seal is positioned proximate the distal end of the housing to substantially seal the housing.

In Example 17, the implantable lead according to Example 16, wherein the fixation helix comprises a helical electrode.

In Example 18, the implantable lead according to Examples 16 or 17, further comprising a low-voltage electrode that is mounted on the body proximal to the helical electrode, and a high-voltage electrode that is mounted on the body proximal to the low-voltage electrode, wherein the body is configured such that the distance between the low-voltage electrode and the high-voltage electrode is about 12 mm.

In Example 19, the implantable lead according to Examples 16-18, further comprising a low-voltage electrode that comprises a flexible coil that is mounted on the body proximal to the helical electrode, and a high-voltage electrode that is mounted on the body proximal to the low-voltage electrode, such that a first portion of the flexible body is located between the flexible coil and the helical electrode and a second portion of flexible body is located between the flexible coil and the high voltage electrode.

In Example 20, the implantable lead according to Examples 16-19, wherein the distal end of the housing comprises a drug-eluting plug.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
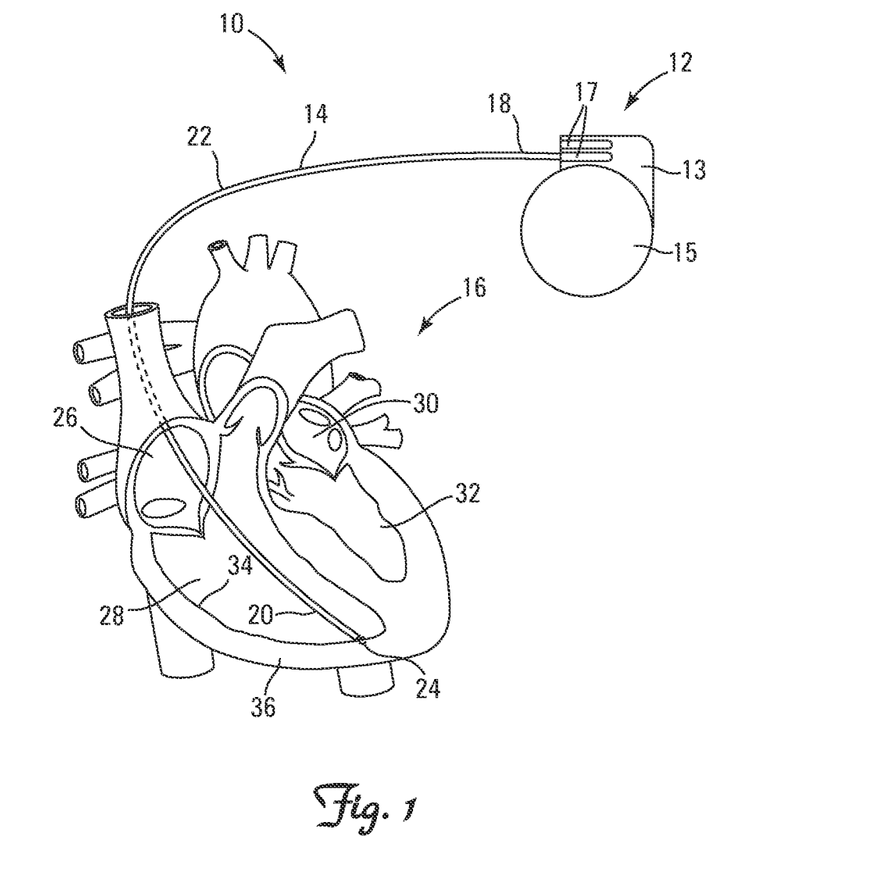
FIG. 1 is a perspective view of an implantable medical device (IMD) in accordance with one embodiment.

FIG. 1 is a perspective view of an implantable medical device (IMD) 10 in accordance with one embodiment. The IMD 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body, or flexible body 22, extending from the proximal region 18 to the distal region 20. The proximal region 18 is coupled to the pulse generator 12 and the distal region 20 is coupled to the heart 16. The distal region 20 includes an extendable/retractable fixation helix 24, which will be discussed in greater detail with respect to subsequent drawings, and which locates and/or secures the distal region 20 within the heart 16. The distal region 20 of the lead 14 has an axially compact design that accommodates a dedicated bipolar electrode configuration. As will be explained in further detail elsewhere and shown in additional figures, the distal region 20 of the lead 14 includes a seal (not shown in FIG. 1) used to seal off an inner lumen (not shown on FIG. 1) of the distal region 20 of the lead 14 from tissue ingrowth. Reduction or prevention of such tissue ingrowth may make retraction of the helix and removal of the lead 14 from the patient's body easier and less traumatic to the patient's surrounding tissue.

The pulse generator 12 typically includes a connector header 13 that couples the pulse generator 12 to the lead 14. The connector header 13 typically contains one or more bores 17 that is/are able to receive a connector (not shown) that is part of a connector assembly (not shown, but see 40 in FIG. 2, discussed below) formed near the proximal region 18 of the lead 14, wherein electrical contacts (not shown) of the header 13 couple with lead contacts (not shown) of the connector assembly (not shown).

The header 13 is attached to a hermetically sealed enclosure 15 that contains a battery, electronic circuitry, and other components known to those skilled in the art. Electrical contacts (not shown) in the header 13 are any type known to those skilled in the art that are electrically connected via feedthroughs (not shown) mounted to extend through the hermetically sealed enclosure 15 in order to electrically couple the lead 14 with pulse generator 12.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from any flexible, biocompatible material suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body 22 characteristics to its intended clinical and operating environments. In various embodiments, proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments as illustrated, the fixation helix 24, located at the distal region 20 of the lead, penetrates through the endocardium 34, and is imbedded within the myocardium 36. In one embodiment, the IMD 10 includes a plurality of leads 14. For example, it may include a first lead 14 adapted to convey electrical signals between the pulse generator 12 and the right ventricle 28, and a second lead (not shown) adapted to convey electrical signals between the pulse generator 12 and the right atrium 26. Additional leads may also be employed. For example, in various embodiments, a coronary venous lead (not shown) may be utilized for stimulating a left atrium 30 and/or a left ventricle 32 of the heart 16.

In the illustrated embodiment shown in FIG. 1, the fixation helix 24 penetrates the endocardium 34 of the right ventricle 28 and is imbedded in the myocardium 36 of the heart 16. In some embodiments, the fixation helix 24 is electrically active and thus can be used to sense the electrical activity of the heart 16 or to apply a stimulating pulse to the right ventricle 28. In other embodiments, the fixation helix 24 is not electrically active. Rather, in some embodiments, other components of the lead 14 are electrically active.

Figure 2:
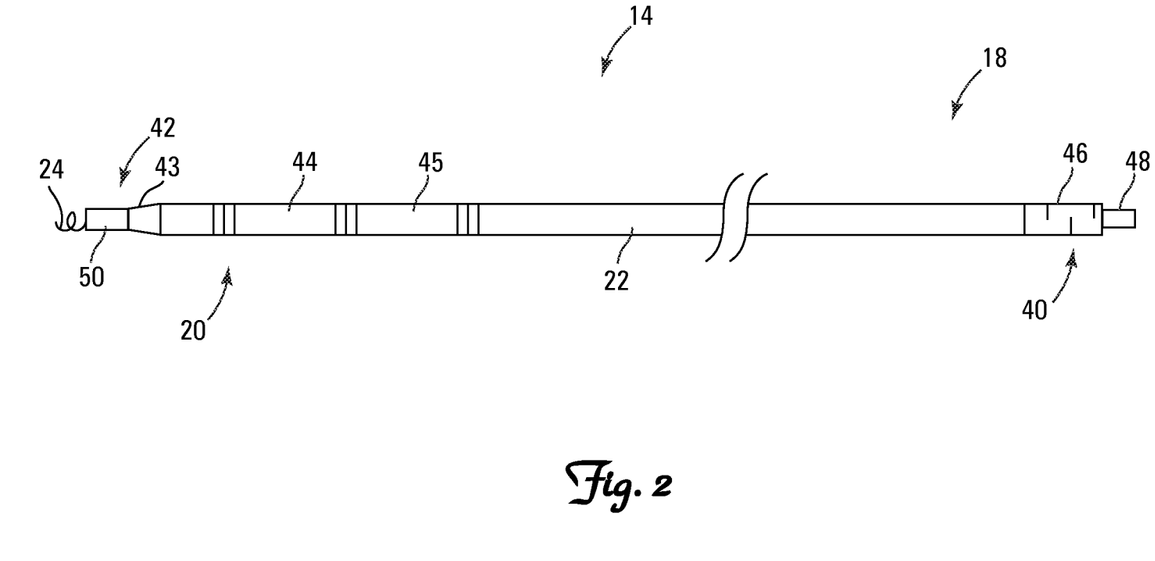
FIG. 2 is a side elevation view of the lead of FIG. 1.

FIG. 2 is an isometric illustration of the lead 14. A connector assembly 40 is disposed at or near the proximal region 18, or proximal end, of the lead 14. The connector assembly 40 includes a connector 46 and a terminal pin 48. The connector 46 is configured to be coupled to the lead body 22 and is configured to mechanically and electrically couple the lead 14 to the header 13 on the pulse generator 12 (see FIG. 1). In various embodiments, the terminal pin 48 extends proximally from the connector 46 and in some embodiments is coupled to a conductor member (not visible in this view) that extends longitudinally through the lead body 22 such that rotating the terminal pin 48 (relative to the lead body 22) causes the conductor member to rotate within the lead body 22. In some embodiments, the terminal pin 48 includes an aperture (not shown) extending therethrough in order to accommodate a guide wire or an insertion stylet.

A distal assembly 42 is disposed at or near the distal region 20 or distal end of the lead 14 or lead body 22. Depending on the functional requirements of the IMD 10 (see FIG. 1) and the therapeutic needs of a patient, the distal region 20 of the lead 14 may include one or more electrodes. In the illustrated embodiment, the distal region 20 includes a single coil electrode, otherwise referred to as a "high-voltage electrode," or a pair of such coil electrodes 44 and 45, as shown, that can function as shocking electrodes for providing a defibrillation shock to the heart 16. In some embodiments, the coil electrodes 44 and 45 include a coating that is configured to control (i.e., promote or discourage) tissue ingrowth. In various embodiments, the lead 14 may include only a single coil electrode. In various other embodiments, the lead 14 also includes one or more low-voltage electrodes (e.g., ring electrodes), such as electrode 43, along the lead body 22 in lieu of or in addition to the coil electrodes 44, 45. When present, the low-voltage electrodes operate as relatively low-voltage, pace/sense electrodes. As will be appreciated by those skilled in the art, a wide range of electrode combinations may be incorporated into the lead 14 within the scope of the various embodiments.

The distal assembly 42 includes a housing 50, within which the fixation helix 24, or helical electrode, is at least partially disposed. As will be explained in greater detail herein, the housing 50 accommodates a mechanism that enables the fixation helix 24 to move distally and proximally relative to the housing 50, but that includes structure (not seen in this view) that limits distal travel of the fixation helix 24 (relative to the housing 50) in order to reduce or prevent over-extension of the fixation helix 24. As noted herein, the fixation helix 24 operates as an anchoring means for anchoring the distal region 20 of the lead 14 within the heart 16.

In some embodiments, the fixation helix 24, or helical electrode, is electrically active, and is used as a low-voltage, pace/sense electrode. In some embodiments, the fixation helix 24 is made of an electrically conductive material such as ELGILOY™, MP35N™, tungsten, tantalum, iridium, platinum, titanium, palladium, stainless steel as well as alloys of any of these materials. In some embodiments, the fixation helix 24 is made of a non-electrically conductive material such as polyethersulfone (PES), polyurethane-based thermoplastics, ceramics, polyetheretherketone (PEEK) and polypropylene, or the helix may be completely or partially insulated with a polymer such as PARYLENE™ to either electrically isolate the helix or to raise pacing impedance. In some embodiments, the fixation helix 24 includes an electroactive coating. Such an electroactive coating, or high surface area coating, may comprise a noble metal oxide, such as iridium oxide (e.g., IROX™), platinum black, titanium nitride, or finely divided carbon, for example.

Figure 3A:
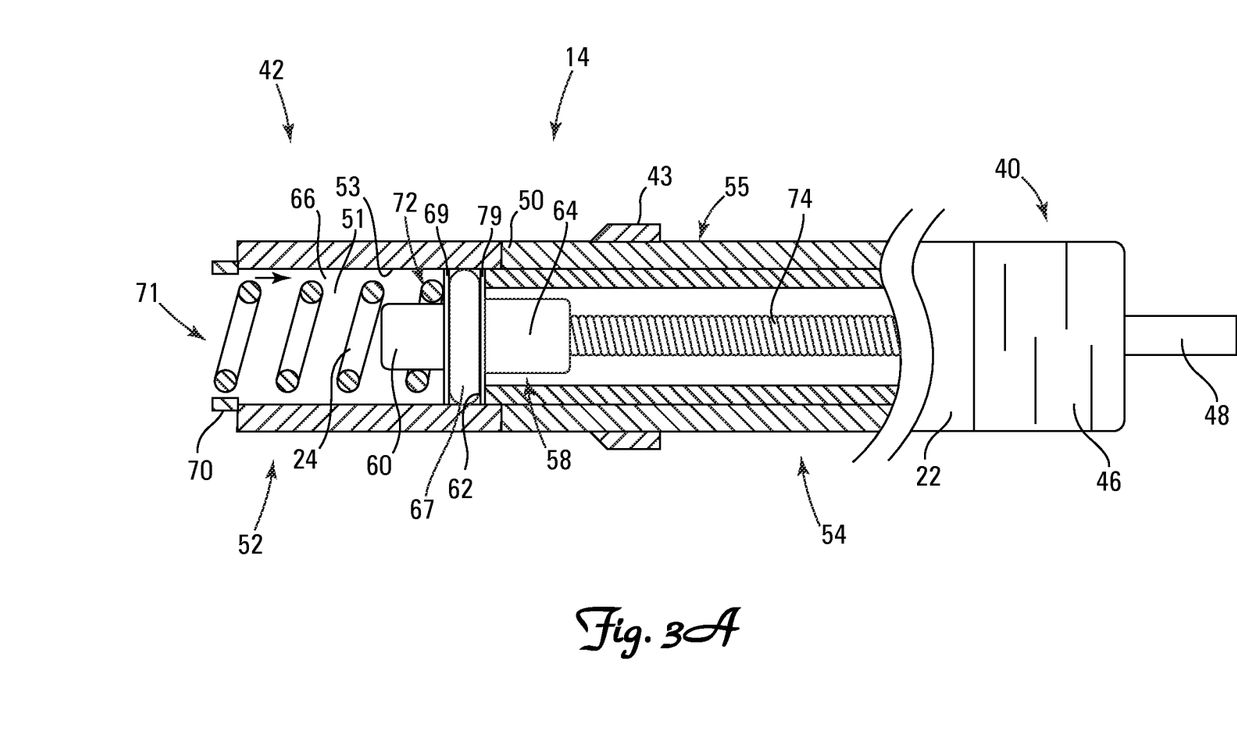
FIG. 3A is a partial cross-sectional view of the lead of FIG. 1 shown in a retracted position.
Figure 3B:
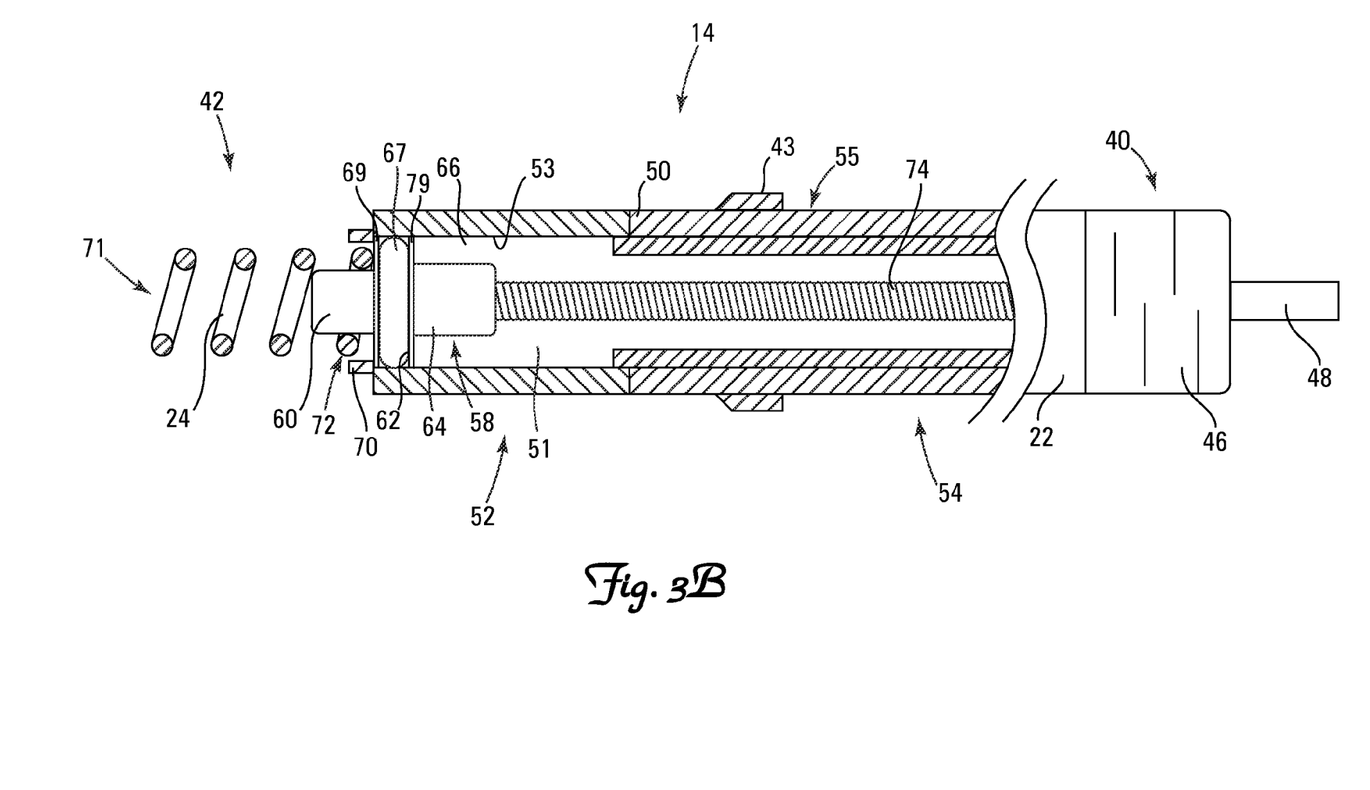
FIG. 3B is a partial cross-sectional view of the lead of FIG. 1 shown in an extended position.
Figure 4:
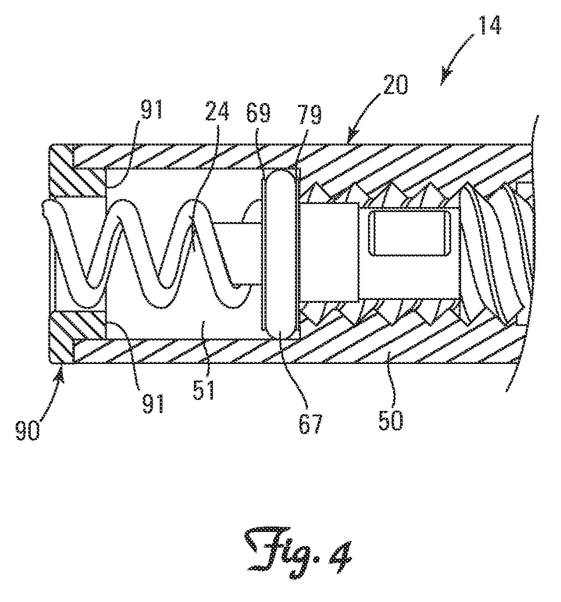
FIG. 4 is a partial cross-sectional view of a lead in accordance with another embodiment.
Figure 5:
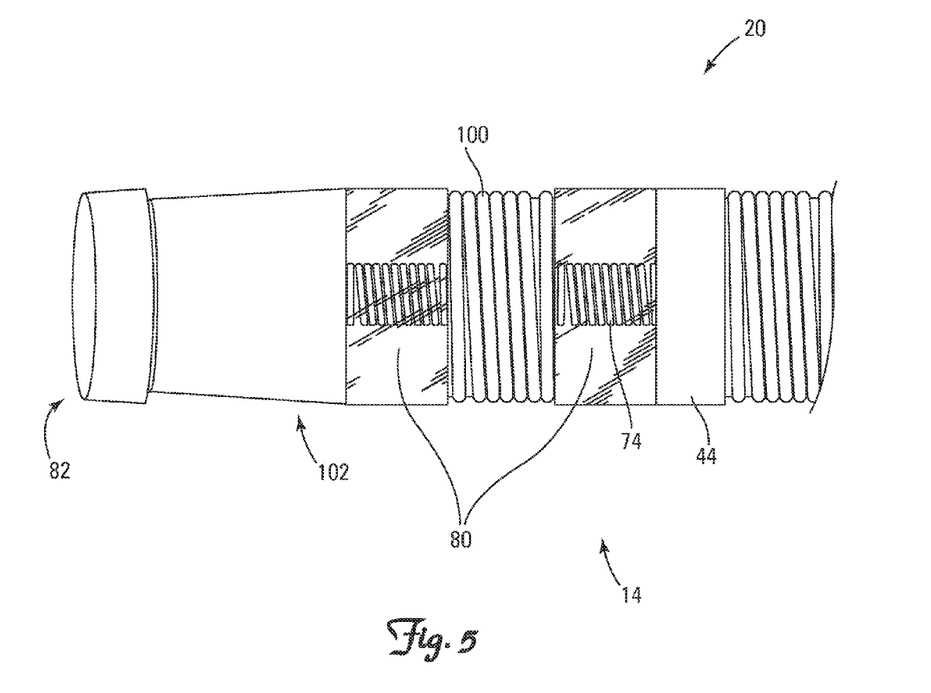
FIG. 5 is a partial perspective view of a lead in accordance with another embodiment.

FIGS. 3-5 illustrate several leads including distal assemblies in accordance with various embodiments. FIG. 3A and FIG. 3B are partial cross-sections of the lead 14 including the distal assembly 42. In FIG. 3A, the fixation helix 24 is illustrated in a retracted position while FIG. 33 illustrates the fixation helix 24 in an extended position. In the illustrated embodiment, the fixation helix 24 is electrically active so as to be operable as a low-voltage, pace/sense electrode.

As shown in FIGS. 3A and 3B, the housing 50 includes a distal region 52 and a proximal region 54. The proximal region 54 of the housing 50, in one embodiment, is fixedly coupled to the distal end of the lead body 22. The housing 50 comprises a wall that has an external surface 55 and an internal surface 53, with the internal surface 53 defining an inner lumen 51. The housing 50 is, in general, relatively rigid or semi-rigid. In some embodiments, the housing 50 is made of an electrically conductive material such as ELGILOY™ MP35N™, tungsten, tantalum, iridium, platinum, titanium, palladium, and stainless steel, as well as alloys of any of these materials. In some embodiments, the housing 50 is made of a non-electrically conductive material such as PES, polyurethane-based thermoplastics, ceramics, polypropylene and PEEK.

As shown, the distal assembly 42 includes a coupler 58. In some embodiments, the coupler 58 is formed of a metallic material and is disposed within the housing 50 and configured to move longitudinally and/or rotationally with respect to the housing 50. The coupler 58 includes a distal portion 60, a proximal portion 64, and a central portion 62. In some embodiments, the proximal portion 64 of the coupler 58 is connected to a conductor member 74 (discussed below). The fixation helix 24 is connected to the distal portion 60 of the coupler 58.

In some embodiments, as illustrated in FIG. 33, the distal portion 60 or the central portion 62 of the coupler 58 may be configured to include a seal 67 to prevent tissue ingrowth into an inner lumen 51 of lead 14 when the fixation helix 24 is in a fully extended position. In some embodiments, the seal 67 is an annular, resilient seal. The seal 67 may comprise an O-ring, for example. In the embodiments in which the seal 67 is an O-ring, as shown in FIG. 3A, the O-ring may be surrounded on both sides by a pair of flanges, with such flanges being a distal flange 69 and a proximal flange 79. The flanges 69, 79 are attached to the coupler 58, and allow the O-ring seal 67 to move with the coupler 58. Other configurations are, however, also contemplated.

The seal 67 may be disposed between the coupler 58 and the housing 50, and may provide an at least substantially fluid-tight seal with the housing 50. The seal 67 may slide along the inner surface 53 of the housing 50 during advancement and/or retraction of the fixation helix 24. The inner surface 53 of the housing 50 may include a sealing groove 66 in which the seal 67 slides and is seated. The sealing grove 66 can extend around the inner circumference of the housing 50 along a distal portion of the housing 50, through which the seal 67 is desired to move.

As shown in FIG. 3B, when the fixation helix 24 is in its fully extended position, the seal 67 seals off the inner lumen 51 of the distal end of the housing 50. When the helix 24 is in its fully extended position, as shown in FIG. 3B, the distal flange 69 is shown contacting a portion of the housing 50 itself. In the particular embodiment shown in FIG. 3B, the housing 50 includes an axial shoulder 70 at the distal end of the housing 50 and extending radially inward relative to the internal surface 53 of the wall of the housing 50. The distal flange 69 proximate the seal 67 contacts the shoulder 70 when the helix 24 is in its fully extended position and seals off the inner lumen 51 of the housing 58 from tissue ingrowth. In other embodiments, the seal 67 itself may contact the shoulder 70, for example, or another portion of the internal wall 53 of the housing 50 proximate the distal end of the distal assembly 42, in order to seal off the inner lumen 51 of the housing 50 from tissue ingrowth.

The fixation helix 24 has a distal region 71 and a proximal region 72. The proximal region 72 is secured to the distal portion 60 of the coupler 58. One or more attachment methods are used to secure the fixation helix 24 to the coupler 58. In some embodiments, the proximal region 72 of the fixation helix 24 is welded or soldered onto the distal portion 60 of the coupler 58. In some embodiments, the proximal region 72 of the fixation helix 24 has an inner diameter that is less than an outer diameter of the distal portion 60 of the coupler 58, and thus is held in place via compressive forces. In some embodiments multiple attachment methods are used.

A conductor member 74 is secured to the proximal portion 64 of the coupler 58, and extends proximally through the lead body 22 and the connector assembly 40. In some embodiments, the conductor member 74 includes or is otherwise formed from a metallic coil. The coupler 58 provides an electrical connection between the conductor member 74 and the fixation helix 24. In the connector assembly 40, the conductor member 74 is coupled to the terminal pin 48 such that rotation of the terminal pin 48 causes the conductor member 74 to rotate. As the conductor member 74 rotates, the coupler 58 and the fixation helix 24 will also rotate. In some embodiments, the fixation helix 24 is rotated via a stylet that is inserted through an aperture (not shown) that may be formed within the terminal pin 48 (FIG. 2). The distal assembly 42 is configured so that relative rotation of the coupler 58 and fixation helix 24 relative to the housing 50 results in longitudinal translation of the coupler 58 and fixation helix 24 relative to the housing 50, thereby providing the extendable/retractable functionality of the fixation helix 24.

The particular arrangement illustrated for facilitating extension and retraction of the fixation helix 24 is exemplary only. In other words, any arrangement, whether now known or later developed, for providing the extendable/retractable functionality of the fixation helix 24 can be utilized in connection with the various embodiments of the present invention.

Another embodiment is shown in FIG. 4. In FIG. 4, instead of seal 67 or distal flange 69 abutting the shoulder 70 formed in the housing 50 (as in the embodiment of FIGS. 3A, 3B), the seal 67 (or distal flange 69) abuts a drug-eluting collar 90 that is disposed at the distal end of housing 50, in order to seal the inner lumen 51 of the housing 50 from tissue ingrowth. The drug-eluting collar 90 may be configured as shown to include a shoulder portion 91 against which the seal 67 will abut when the fixation helix 24 is in a fully extended position. The drug-eluting collar 90, while the helix 24 is retracted, may enclose the inner lumen 51. The helix 24 may screw through the drug-eluting collar 90 as it is extended. In other embodiments, the drug-eluting collar may comprise a ring shape that surrounds the distal end or opening of the housing 50.

The inclusion of the shoulder 91 on the drug-eluting collar 90 as a surface against which the seal 67 or distal flange 69 abuts allows for a simplified process for making the distal assembly 42. That is, with such a configuration, the housing 50 can be formed in one piece and the other components of the distal assembly can be inserted into the distal opening into the inner lumen 51 prior to placing the drug eluting collar 90. This is in contrast to the embodiments of FIGS. 3A and 3B, which may require the housing 50 to be constructed in two pieces to facilitate construction of the distal assembly.

The drug eluting collar 90 may comprise a material that is soft. Advantageously, such a soft distal portion of the lead 14 provided by the drug eluting collar 90 may reduce peak tissue stress as the lead 14 is implanted into a patient. An example of such a soft material is an elastomer, such as scone. Although other materials are also contemplated.

The drug eluting collar 90 may also provide a time-released dosage of a therapeutic material or drug that elutes over time having a desirable effect on surrounding cardiac tissues. The therapeutic material may be, for example, a steroid or other anti-inflammatory agent. The drug eluting collar 90 may be formed from a compound that includes an elastomer (e.g., scone) and about 15% to about 50% by weight of the therapeutic material. Preferably, the therapeutic material is a steroid. However, other therapeutic drugs or agents may be employed. In use, the steroid elutes from the elastomer over time having a desirable effect on surrounding cardiac tissue. The geometry and dimensions of the collar 90 may be modified in order to control the rate at which the steroid is eluted (e.g., from the silicone). Suitable steroids include dexamethasone sodium phosphate and dexamethasone sodium acetate. Other steroids may also be used.

In some embodiments, and as shown in FIGS. 2, 3A and 3B, the distal region 20 of the lead 14 may include an additional low-voltage (e.g., ring) electrode 43 between the distal-most shocking coil 44 and the distal assembly 42. Such a lead is a tri-polar lead because it is configured with a tip electrode (i.e., the fixation helix 24), a ring electrode 43 and a coil electrode 44 (actually includes two coil electrodes 44, 45), or is otherwise known as a "dedicated bipolar lead."

Due to the presence of the plurality of electrodes at or near the distal end of a dedicated bipolar lead, and particularly addition of a ring electrode (e.g., the electrode 43) in a dedicated bipolar design, the length of a stiffer distal portion of the lead may be increased relative to a lead lacking such a dedicated ring electrode. An increase in the length of a stiff distal portion may not be desired for various reasons. One reason, for example, is that the distal region 20 with electrodes, is stiffer than more proximal regions of the lead 14 that are more flexible and do not include such features. Including a longer, stiffer distal region in a lead may make the distal region more difficult to maneuver through tissue and vasculature during implantation. Thus, in some embodiments, the axially compact design of the distal assembly 42 advantageously accommodates a dedicated bipolar lead design. Generally, a desired distance between the distal-most tip of the lead and the distal-most portion of the distal-most shocking electrode is about 0.5 inches (12.7 mm). In the various embodiments utilizing the distal assembly 42 described herein, the dedicated bipolar electrode can be located within about 0.5 inches (12.7 mm) from the distal tip of the lead.

Flexibility of the distal region 20 of the lead 14 is important for successful maneuvering and placement of the distal region 20 of the lead 14 within the heart 16. Addition of more electrodes in the distal region, for example the ring electrode 43 in FIG. 3B, may increase the stiffness of the distal region 20. Tip flexibility is important for vascular passage, positioning and reducing pressure at a fixation site. Thus, in some embodiments, the distal region 20 of the lead is configured to have a relatively high degree of flexibility relative to the embodiments of FIGS. 3A and 3B.

FIG. 5 illustrates the distal portion 20 of the lead 14 having a dedicated bi-polar configuration. The embodiment shown in FIG. 5 is in many respects similar or identical to the embodiments illustrated in and described with respect to FIGS. 3A-3B and FIG. 4, except as described herein. The embodiment of FIG. 5 includes first and second flexible portions 80 and a flexible low-voltage electrode 100, in the form of a coil. Components are arranged along the distal portion 20, from proximal-most location to distal-most location, with a shocking coil, or high-voltage electrode 44, then the first flexible portion 80, then the flexible, low-voltage electrode 100, then the second flexible portion 80, then a distal assembly 102, which includes in various embodiments a fixation helix (not visible in FIG. 5) that can be extended from a distal tip 82. The configuration of the embodiment of FIG. 5 is one example, and others are also contemplated.

The flexible portions 80 provide enhanced flexibility to counteract stiffening caused by addition of a ring electrode necessary for a dedicated bi-polar lead design. In FIG. 5, the flexible, or articulating, portions 80 are thus placed along the length of the distal region 20 of the lead 14. The flexible portions 80 may comprise a material made from silicone, polyurethane, another flexible biocompatible polymer or a combination thereof. The conductor member 74 may be visible through the flexible portions 80, as shown.

Addition of the flexible portions 80, as in FIG. 5 can also increase the length of the distal region 20 of the lead 14, and also increase the distance between the tip electrode, or fixation mechanism (such as 24 in FIG. 2 that may extend from a distal tip 82), and the coil electrode 44. Such an increase in distance can result in increasing defibrillation thresholds. Thus, the various embodiments can include a relatively axially compact distal region 20 (e.g., by including the embodiments of the distal assembly 42 described herein) which can allow for inclusion of flexible portions 80 in the lead 14 without having to increase defibrillation thresholds to an undesirable level. Other shortened configurations besides those shown and described herein are also contemplated by the present invention.

In one embodiment, the implantable lead comprises a low-voltage electrode that is mounted on the body proximal to a helical or fixation electrode, and a high-voltage electrode that is mounted on the body proximal to the low-voltage electrode. The body is then configured such that the distance between distal tip 82 and the proximal-most portion of the proximal-most high-voltage electrode 44 is about 12 mm. The distance between the distal tip 82 and the distal-most portion of the low-voltage electrode 100 is about 8 mm. However, other distances are contemplated.

In the embodiment illustrated in FIG. 5, the flexible low-voltage electrode 100 is provided in lieu of the relatively rigid low voltage ring electrode 43 between the fixation helix 24 and the distal most shocking coil electrode 44 as shown in FIG. 2. In the illustrated embodiment, the flexible low-voltage electrode 100 may comprise a spring or coil. In other embodiments, the low-voltage electrode 100 could be micro-machined, laser-cut or etched in order to impart flexibility to the electrode. The flexible low-voltage electrode 100 may comprise any suitable material, such as ELGILOY™, MP35N™, tungsten, tantalum, iridium, platinum, titanium, palladium, and stainless steel, as well as alloys of any of these materials. The flexible low-voltage electrode 100 provides still further flexibility as compared to a dedicated bi-polar lead utilizing a rigid ring electrode between the lead tip and the distal most shocking coil.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable lead comprising:
   a flexible body extending between a proximal end and a distal end; and
   a distal assembly coupled to the distal end of the body and including:
      a housing having a wall having an external surface and an internal surface defining an inner lumen, a distal end and a proximal end, the proximal end fixedly coupled to the distal end of the body, the housing having an axial shoulder extending radially inward relative to the internal surface at or near the distal end of the housing;
      a coupler rotatably disposed within the housing, the coupler having a proximal end and a distal end;
      a helical electrode fixedly secured to the distal end of the coupler, wherein the coupler and the helical electrode are configured to translate relative to the housing between a retracted position and a fully extended position; and
      a resilient seal fixedly secured to the coupler between the proximal and distal ends thereof and able to translate with the coupler relative to the housing, the seal positioned to sealingly engage the internal surface of the housing wall, wherein when the helical electrode is in the fully extended position, the seal is positioned proximate the shoulder of the housing to substantially seal off the inner lumen of the housing.

2. The implantable lead of claim 1, wherein the seal is in contact with the shoulder when the helical electrode is in the fully extended position.

3. The implantable lead of claim 1, further comprising a groove in the inner surface of the housing wall, and a distal flange and a proximal flange attached to the coupler that surround the seal, wherein the seal sits in the groove, and when the conductor member is translated such that the helical electrode is in the fully extended position, the distal flange is in contact with the shoulder of the housing.

4. The implantable lead of claim 1, wherein the seal comprises an O-ring.

5. The implantable lead of claim 1, further comprising a low-voltage electrode that is mounted on the body proximal to the helical electrode, and a high-voltage electrode that is mounted on the body proximal to the low-voltage electrode, wherein the body is configured such that the distance between the low-voltage electrode and the high-voltage electrode is about 12 mm.

6. The implantable lead of claim 1, further comprising a low-voltage electrode that comprises a flexible coil that is mounted on the body proximal to the helical electrode, and a high-voltage electrode that is mounted on the body proximal to the low-voltage electrode, such that a first portion of the flexible body is located between the flexible coil and the helical electrode and a second portion of flexible body is located between the flexible coil and the high voltage electrode.

7. The implantable lead of claim 1, wherein the seal provides an at least substantially fluid-tight seal with the housing.

8. An implantable lead comprising:
a flexible body extending between a proximal end and a distal end; and
a distal assembly coupled to the distal end of the body and including:
a housing having a wall having an external surface and an internal surface defining an inner lumen, a distal end and a proximal end, the proximal end fixedly coupled to the distal end of the body;
a coupler rotatably disposed within the housing, the coupler having a proximal end and a distal end;
a drug-eluting collar disposed at the distal end of the housing and including a portion extending radially inward relative to the internal surface of the housing wall;
a helical electrode fixedly secured to the coupler, wherein the coupler and the helical electrode are configured to translate relative to the housing between a retracted position and a fully extended position; and
a resilient seal fixedly secured to the coupler between the proximal and distal ends thereof and able to translate with the coupler relative to the housing, the seal positioned to sealingly engage the internal surface of the housing wall, wherein when the helical electrode is in the fully extended position, the seal is positioned proximate the drug-eluting collar to substantially seal off the inner lumen of the housing.

9. The implantable lead of claim 8, wherein the seal is in contact with the drug-eluting collar when the helical electrode is in the fully extended position.

10. The implantable lead of claim 8, further comprising a groove in the inner surface of the housing wall, and a distal flange and a proximal flange attached to the coupler that surround the seal, wherein the seal sits in the groove, and when the conductor member is translated such that the helical electrode is in the fully extended position, the distal flange is in contact with the drug-eluting collar.

11. The implantable lead of claim 8, wherein the seal comprises an O-ring.

12. The implantable lead of claim 8, further comprising a low-voltage electrode that is mounted on the body proximal to the helical electrode, and a high-voltage electrode that is mounted on the body proximal to the low-voltage electrode, and the body is configured such that the distance between the low-voltage electrode and the high-voltage electrode is about 12 mm.

13. The implantable lead of claim 8, further comprising a low-voltage electrode that comprises a flexible coil that is mounted on the body proximal to the helical electrode, and a high-voltage electrode that is mounted on the body proximal to the low-voltage electrode, such that a first portion of the flexible body is located between the flexible coil and the helical electrode and a second portion of flexible body is located between the flexible coil and the high voltage electrode.

14. The implantable lead of claim 8, wherein the drug-eluting collar comprises an elastomer and a steroid.

15. The implantable lead of claim 8, wherein the seal provides an at least substantially fluid-tight seal with the drug-eluting collar.

16. An implantable lead configured to carry an electrical signal, the implantable lead comprising:
a flexible body extending between a proximal end and a distal end, the body configured to carry an electrical signal from the proximal end to the distal end; and
a distal assembly coupled to the distal end of the body and including:
a housing having a distal region and a proximal region, the proximal region fixedly coupled to the distal end of the body, the distal region including a distal end;
a coupler rotatably disposed within the housing, the coupler having a proximal region and a distal region;
a fixation helix attached to the coupler and able to translate with the coupler from a retracted position to a fully extended position;
a low-voltage electrode that comprises a flexible coil that is mounted on the body proximal to the fixation helix; and
a resilient seal disposed on the coupler and between the coupler and the housing that is able to translate with the coupler relative to the housing and sealingly engage the housing, wherein when the coupler is translated such that the fixation helix is in the fully extended position, the seal is positioned proximate the distal end of the housing to substantially seal the housing.

17. The implantable lead of claim 16, wherein the fixation helix comprises a helical electrode.

18. The implantable lead of claim 17, further comprising a high-voltage electrode that is mounted on the body proximal to the low-voltage electrode, wherein the body is configured such that the distance between the low-voltage electrode and the high-voltage electrode is about 12 mm.

19. The implantable lead of claim 17, further comprising a high-voltage electrode that is mounted on the body proximal to the low-voltage electrode, such that a first portion of the flexible body is located between the flexible coil and the helical electrode and a second portion of flexible body is located between the flexible coil and the high voltage electrode.

20. The implantable lead of claim 16, wherein the distal end of the housing comprises a drug-eluting plug.

\* \* \* \* \*